(12) United States Patent
Lesage (10) Patent No.: US 8,202,087 B2
(45) Date of Patent: Jun. 19, 2012

(54) GRINDING TIP FOR A VIBRATIONAL DENTAL INSTRUMENT

(76) Inventor: Patrick Lesage, Saint Malo (FR)

( * ) Notice: Subject to any disclaimer, the term of this patent is extended or adjusted under 35 U.S.C. 154(b) by 188 days.

(21) Appl. No.: 11/665,784

(22) PCT Filed: Oct. 20, 2005

(86) PCT No.: PCT/FR2005/050871
§ 371 (c)(1),
(2), (4) Date: Jan. 28, 2008

(87) PCT Pub. No.: WO2006/043007
PCT Pub. Date: Apr. 27, 2006

(65) Prior Publication Data
US 2009/0047623 A1    Feb. 19, 2009

(30) Foreign Application Priority Data

Oct. 20, 2004   (FR) ...................................... 04 11129

(51) Int. Cl.
*A61C 1/07*   (2006.01)
(52) U.S. Cl. ...................................................... 433/118
(58) Field of Classification Search .................. 433/118, 433/119, 114, 146, 147, 165
See application file for complete search history.

(56) References Cited

U.S. PATENT DOCUMENTS

| 4,283,175 | A |   | 8/1981  | Nash |
| 4,289,486 | A | * | 9/1981  | Sargeant ........................ 433/118 |
| 4,609,352 | A | * | 9/1986  | Riitano ........................... 433/102 |
| 6,062,858 | A |   | 5/2000  | Hugo et al. |
| 6,186,789 | B1 |  | 2/2001  | Hugo et al. |
| 6,312,256 | B1 |  | 11/2001 | Dieras et al. |
| 6,910,889 | B1 | * | 6/2005 | Hickok ........................... 433/119 |

* cited by examiner

*Primary Examiner* — Sunil K Singh
(74) *Attorney, Agent, or Firm* — Bacon & Thomas, PLLC (57) ABSTRACT

Vibratory tip (100) including a body (110) having a first end (111) adapted to be mechanically coupled rigidly with a surgical handpiece (101) generating vibrations and a second end to which there is fixed a tool holder (112) intended to reproduce the vibrations transmitted by the handpiece. The tip furthermore includes a tool (120) with a working area (121). The tool (120) is freely rotatably mounted relative to the tool holder (112), which allows the tool to adjust itself automatically in order to remain in contact with the tooth and position the working area on the entire periphery of the tooth with a single tip. The tool preferably includes two working areas to improve keeping and guiding the tool on the surface of the tooth to be treated.

14 Claims, 8 Drawing Sheets

GRINDING TIP FOR A VIBRATIONAL DENTAL INSTRUMENT

FIELD AND BACKGROUND OF THE INVENTION

The present invention concerns dental treatment instruments and more particularly vibrational instruments, such as scaling instruments, which comprise instruments vibrating at audible or ultrasonic frequencies.

Figure 1A:
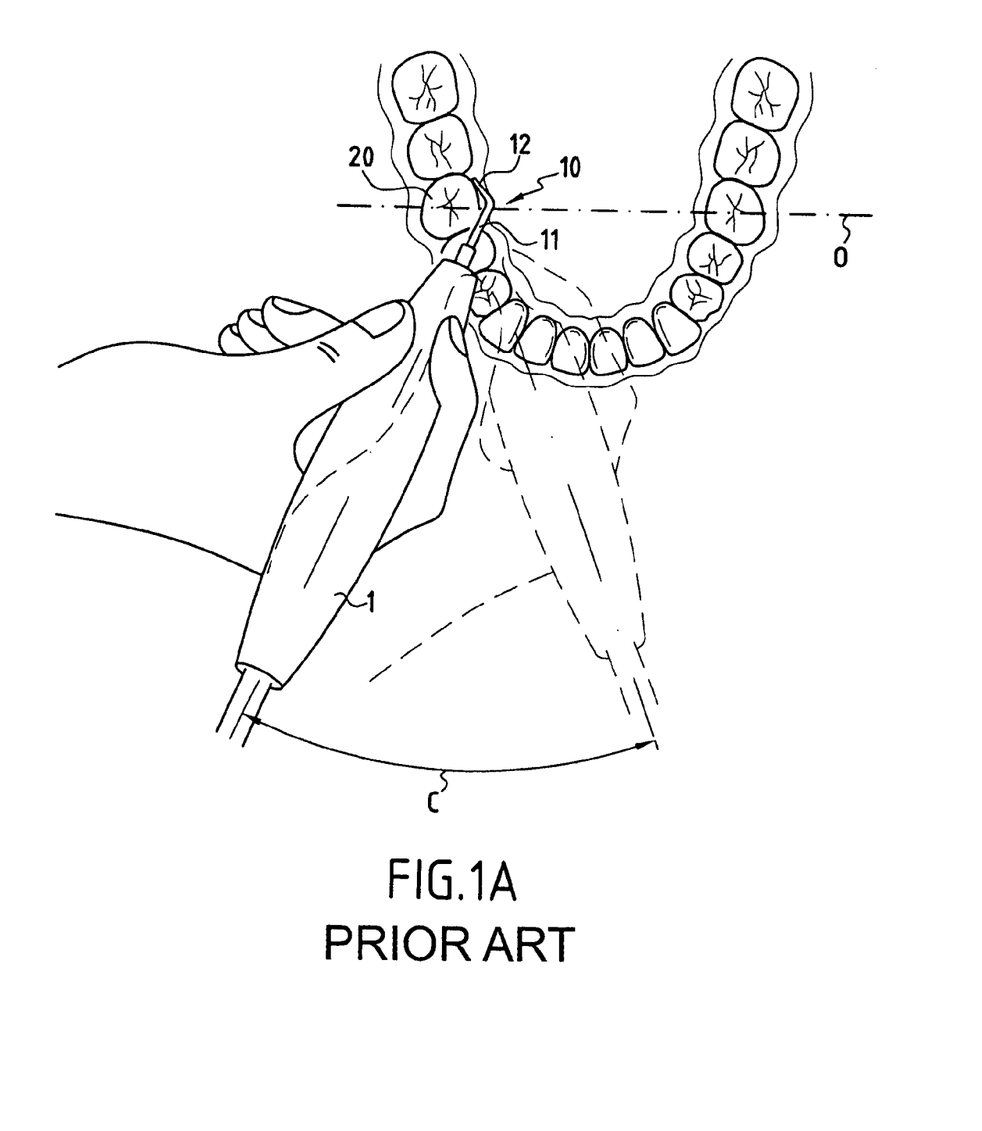
FIG. 1A is a perspective view showing the limits of movement with an asymmetrical tip of the prior art.

This type of instrument, depicted in FIG. 1A, is essentially made up of a handpiece 1 comprising a transducer mechanically coupled rigidly to a vibrating instrument called a "tip" 10, the handpiece being connected to a vibration generator (not depicted). Examples of such tips are described in particular in the documents U.S. Pat. No. 6,312,256 and U.S. Pat. No. 4,283,175.

The tip is an interchangeable part that has a great variety of shapes depending on the use for which it is intended (e.g. scaling: elimination of solid deposits, polishing: elimination of biofilms, grinding: cavities or prosthesis preparations).

As illustrated in FIG. 1A, the existing devices comprise a body 11, most often metallic, one end thereof being assembled rigidly to the transducer of the handpiece 1, the other end of the body 11 being extended by a tool holder itself extended by a tool 12 fixed to the body. This tool comprises a working area that can be a sharp edge, a smooth edge or a smooth surface able to be associated with an abrasive suspension, or else a diamond-charged surface. The vibrations produced by the transducer are thus transmitted directly to the working area of the tool.

So as to be able to be used on all faces of the teeth, the tips are often offered in three shapes: straight, left-hand and right-hand. During a tooth-grinding operation, in particular with a view to a peripheral preparation, the practitioner must use at least two different models of tip: a right-hand and a left-hand.

This is because, owing to the limit of opening of the mouth of the patient and the lateral closure of this cavity by the cheeks which is delimited in FIG. 1A by a line O, the tip must be angled and its movement around the tooth to be ground is relatively limited. The double-ended arrow C shown in FIG. 1A depicts the maximum travel over which the practitioner can move the handpiece 1.

Consequently, during an operation concerning the entire periphery of the tooth, such as for example the peripheral grinding of a tooth 20 aiming to prepare the latter for example for the fitting of a prosthesis (e.g. a crown), the practitioner must use at least two tips: an tip adapted to position the working area of the tool on the front part of the tooth and another tip to position the working area on the back part of the tooth.

Figure 1B:
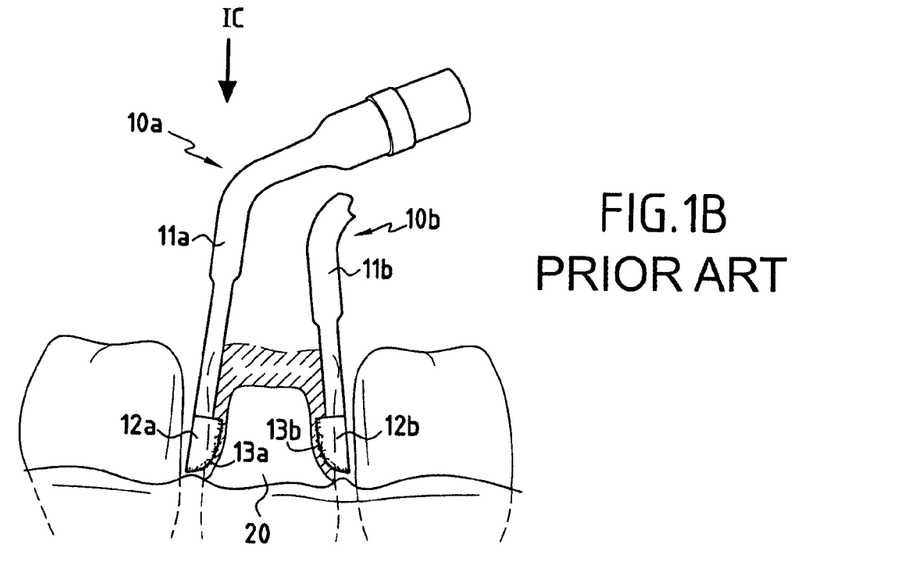
FIG. 1B is a view partially in section which illustrates the necessity of using at least two different tips during peripheral grinding of a tooth according to the prior art.
Figure 1C:
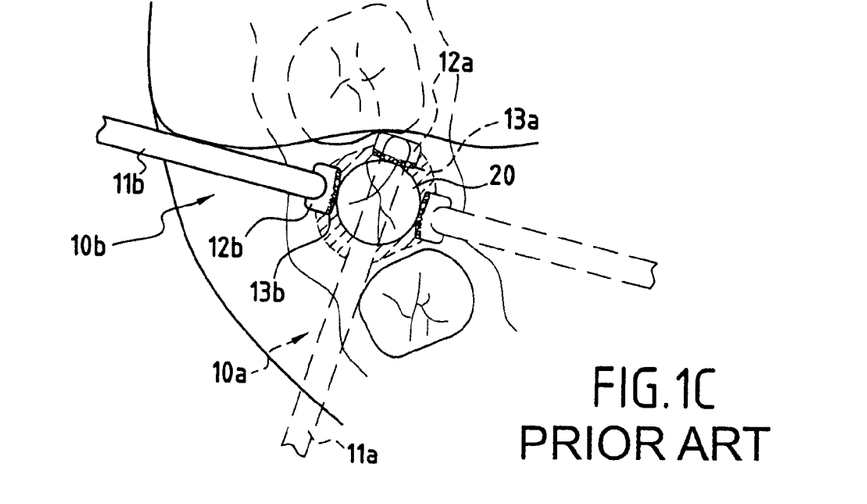
FIG. 1C is a top view of FIG. 1B illustrating the necessity of using at least two different tips during peripheral grinding of a tooth according to the prior art.

More precisely, as depicted in FIGS. 1B and 1C, the practitioner uses a first tip 10a comprising an angled body 11a with the working area 13a of the tool oriented towards the inside so as to be able to grind the back part of the tooth 20 with the working area 13a of the tool 12a and a second tip 10b with an angled body 11b making it possible to grind the front part of the tooth with a working area 13b of the tool 12b turned towards the outside.

Figure 2A:
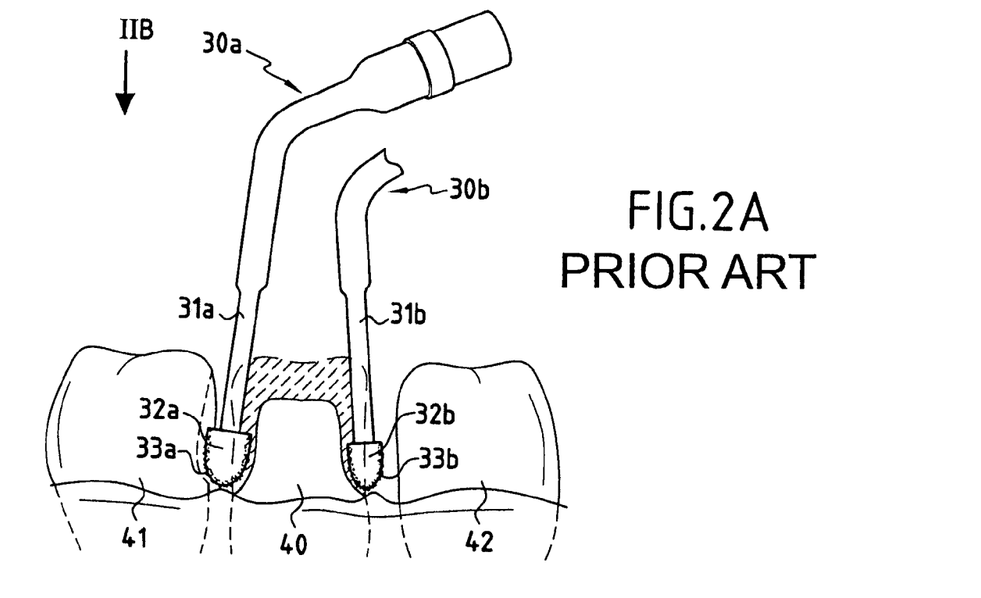
FIG. 2A is a view partially in section of a grinding operation carried out with axisymmetrical tips of the prior art.
Figure 2B:
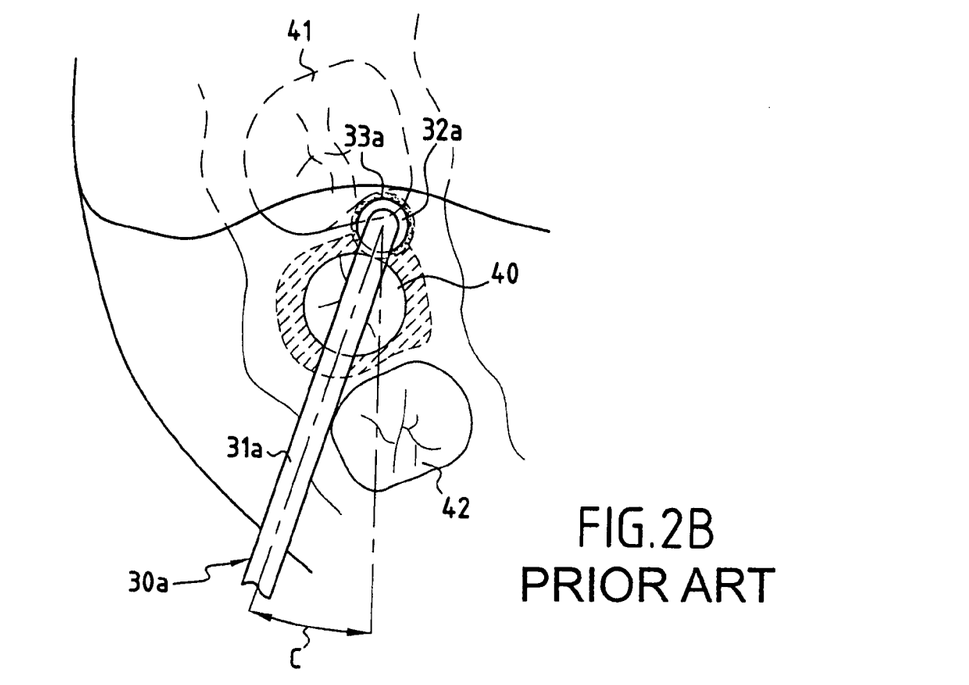
FIG. 2B is a top view of a grinding operation carried out with an axisymmetrical tip according to the prior art.

In order to avoid having to use two tips during peripheral grinding of a tooth, another solution consists of using a single tip with an axisymmetrical working area. Examples of such a tip are depicted in FIGS. 2A and 2B which show two tips 30a and 30b of different dimensions whereof the body 31a, respectively 31b, is extended by a tool holder and a tool 32a, respectively 32b, having an axisymmetrical working area 33a, respectively 33b, comprising a diamond-charged surface over its entire circumference. Thus, it is possible for the practitioner to carry out peripheral grinding of a tooth 40 with one and the same tip.

Although this solution allows peripheral grinding without requiring too great a travel in the angular movement of the axis of the body of the tip, it has however significant drawbacks. This is because, as illustrated in FIGS. 2A and 2B, owing to the axisymmetrical nature of the working area 32a of the tip, and on account of the latter having to have a rotational shape whereof the section reproduces the preparation shape sought, the tool must have a diameter equal to twice the depth of the grinding, that is twice as large as the width of an asymmetrical tool. In this case, either the tip is unusable, or there is a great risk of attacking part of the adjacent teeth 41, 42.

One solution can consist of using a tool 23b of reduced diameter. However, the use of such an tip considerably reduces the depth of grindings that can be carried out without totally eliminating the risks of damaging the teeth 41 and 42.

Moreover, irrespective of the type of tip used, there exist axial vibrations that bring about shocks in the region of the end of the working area. These shocks can lead to a poor surface condition of the worked parts.

Consequently, the use of vibratory tips, whether asymmetrical or axisymmetrical, in particular for peripheral grinding operations, proves relatively difficult and in this field has few advantages compared with the usual rotary instrumentation techniques.

OBJECT AND SUMMARY OF THE INVENTION

The aim of the present invention is to propose a design that makes it possible to position the working area of the tool on all peripheral parts of a tooth, crown or root, with one and the same tip, with no risk of damage to the adjacent teeth. This aim is achieved by virtue of a vibratory tip which, in accordance with the present invention, comprises a tool which is mounted able to rotate freely with the end of the tool holder which is fixed to the body of the tip and which reproduces the vibrations transmitted by the handpiece with which the body of the tip is coupled.

Thus, the tip according to the invention has a design that makes it possible to disassociate the tool from the rest of the body of the tip which is coupled to the handpiece. Since it is able to rotate freely around the body of the tip, the tool adjusts itself automatically (i.e. turns) in order to remain in contact with the tooth so that it is possible to position the working area on the entire periphery of a tooth with a single tip.

The tool furthermore comprises two working areas for guiding and keeping the tool in contact with the surface of the tooth to be treated. This is because the fact of having two working areas on the tool which is able to rotate freely makes it possible to work with two distinct bearing points at the surface of the tooth. Thus, during the movement of the tool over the tooth, the two working areas help the tool to remain in contact with the tooth with great stability since the pressure exerted by the practitioner on the handpiece is distributed between the two working areas, which results in the tool being kept securely on the tooth even during its movement.

The other parts of the tool are preferably smooth in order to protect the adjacent teeth. The working areas can be treated or covered with an abrasive material such as diamond. The working areas preferably have a shape that corresponds to the envisaged treatment (grinding, scaling, polishing, etc.).

In accordance with one embodiment of the invention, the tool comprises in its lower part at least one guide pin for limiting the depth of penetration of the tool. The guide pin can be formed by a piece fixed on the tool, or by an end portion of the tool holder passing through the bottom of the cavity of the tool.

The tool is a preferably detachable and interchangeable element that comprises a bore forming a cavity cooperating with the tool holder, a means of attaching to the tool holder leaving the tool able to rotate freely, one or more working parts which can be a sharp edge, a smooth edge, a smooth surface, an abrasive surface, or a surface treated mechanically, chemically or thermally.

According to one embodiment of the invention, the means of attaching the tool to the tool holder comprise at least one rod whereof the end cooperates with retaining means made on the tool holder.

The tool can be interchangeable with the result that one and the same tip body can be used with different tools.

According to one aspect of the invention, the tool comprises a cavity forming a housing for the tool holder. A pellet made of flexible material can be disposed in the bottom of the cavity in order to cushion the shocks or the effects of any impacts between the end of the tool holder and the tool.

Another object of the present invention is a sound-vibration dental treatment instrument comprising at least one surgical handpiece connected to a vibration generator, characterised in that it furthermore comprises at least one tip as described previously.

BRIEF DESCRIPTION OF THE DRAWINGS

Other characteristics and advantages of the invention will emerge from the following description of particular embodiments of the invention, given by way of non-limiting examples, with reference to the accompanying drawings, in which.

DETAILED DESCRIPTION OF EMBODIMENTS OF THE INVENTION

Figure 3:
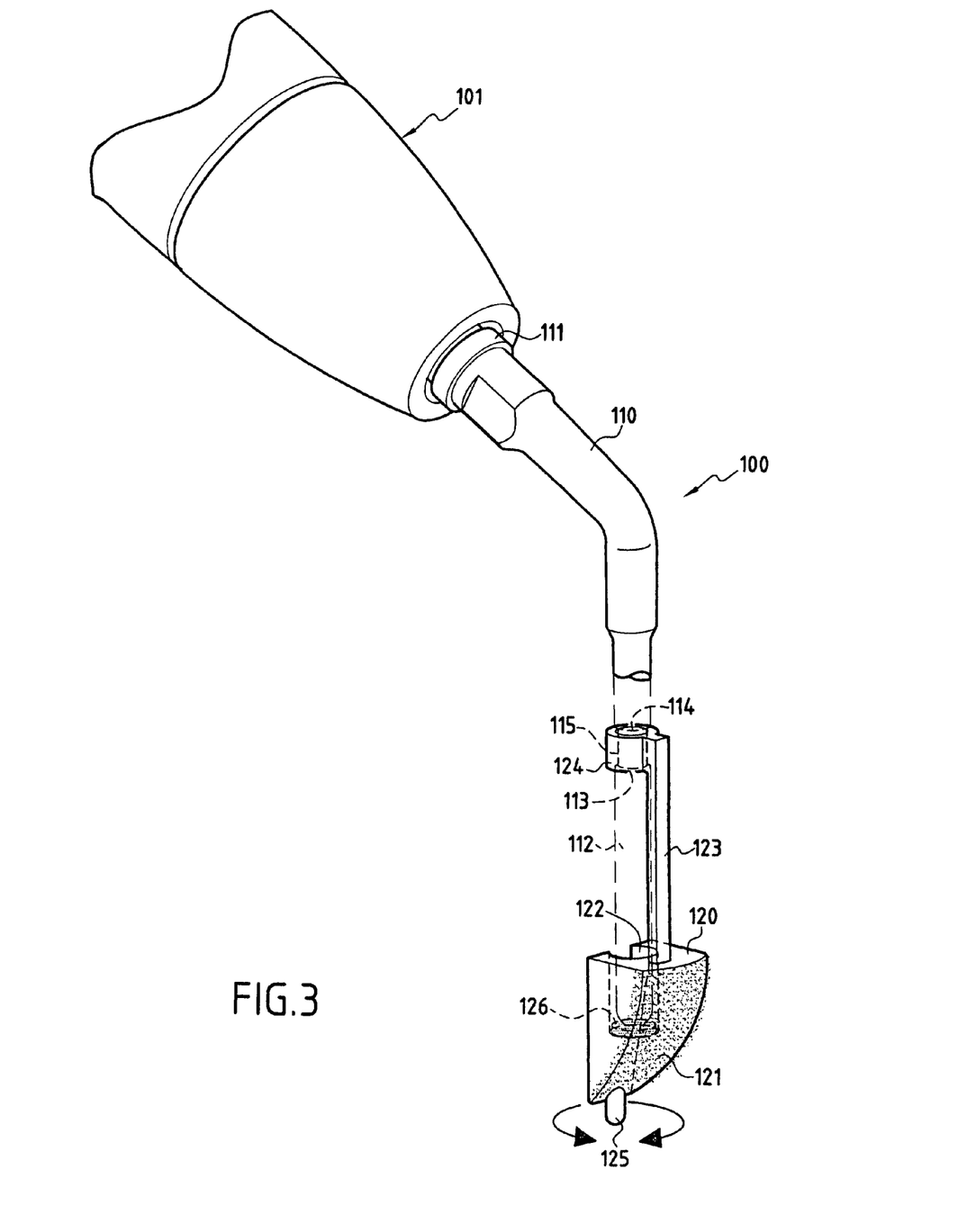
FIG. 3 is a perspective view of a tip in accordance with one embodiment of the invention.

FIG. 3 illustrates a tip 100 in accordance with a first embodiment of the present invention. The tip 100 comprises a body 110 made up of a single piece, for example made of metal, which has a first end 111 adapted to be fixed to a handpiece 101. In a well-known manner, the handpiece 101 is a sound or ultrasound vibration generator which can comprise a transducer (not depicted) formed for example from a piezoelectric material and mechanically coupled rigidly to the tip so as to transmit vibratory waves thereto. The second end of the body 110 forms a tool holder 112 which is intended to reproduce the vibrations transmitted by the handpiece. The tool holder 112 is rigidly assembled with the body of the tip 110 (nut and bolt system, welding or simple extension of the tip).

In accordance with the invention, a tool 120 is disposed at the tool holder 112. The tool 120 comprises a cavity 122 serving as a housing for the end of the tool holder 112. The tool 120 is connected to the tool holder 112 by means of a rod 123 fixed to a ring 124 which makes it possible, by bearing on a shoulder 113, to limit the translational movements of the tool on the tool holder. In the embodiment presented in FIG. 3, the tool holder 112 comprises a second shoulder 114 which forms with the shoulder 113 an annular groove 115 wherein the ring 124 comes to be accommodated. However, retaining of the ring 124 could be provided by a simple collar disposed on the tool holder 112 at the shoulder 113 preventing the tool from escaping from the end of the tool holder, the bottom of the cavity 122 then serving as a limit stop in order to limit the rise of the tool on the tool holder.

As will be described later, other forms of means of attaching the tool onto the tool holder can be envisaged. In general terms, any type of means making it possible to mount the tool able to rotate freely with the tool holder is liable to be suitable for the present invention.

Depending on the circumstances, the rotation of the tool around the tool holder can be total or else limited to an angular range determined by the positioning of limit stops.

In accordance with the present invention, the tool holder 112 of the tip 100, which usually corresponds to the tool, is here housed in the cavity 122 of the tool 120. Through this mounting, the vibrations reproduced at the end of the tool holder 112 are transmitted to the tool 120 and more particularly to the working area 121 of the tool. Thus, unlike the tips of the prior art wherein the working part is totally fixed to the body of the tip, the tip according to the invention comprises a rotationally movable element driven by the vibrations of the end of the tool holder 112.

Optionally, a pellet 126 made of flexible material (e.g. soft metal or elastomer) can be disposed in the bottom of the cavity 122 in order to cushion the shocks or the movements of impacts between the end of the tool holder 112 and the tool 120.

The tool 120 comprises a working area 121 intended to come into contact with the wall of the tooth to be ground or treated (scaling, polishing, etc.). To that end, the working area 121 can be covered with an abrasive material such as diamond or else be smooth and possibly used in association with a solution containing abrasive particles. The shape of the tool 120 and more particularly that of the working area 121 is a function of the grinding profile or of the treatment it is wished to carry out on the tooth.

Figure 4:
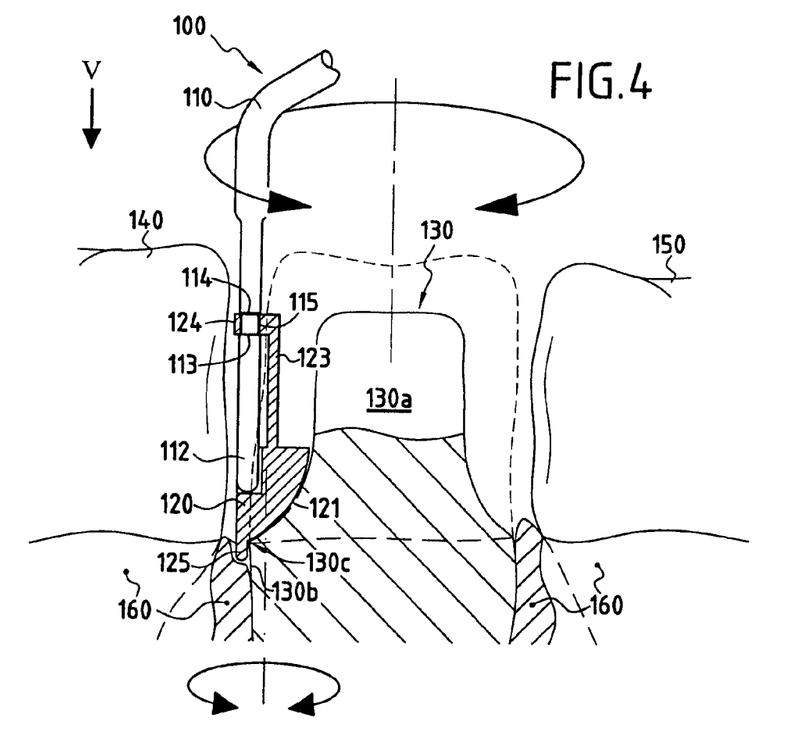
FIG. 4 is a view partially in section showing the tip of FIG. 3 during a grinding operation.

The other parts of the tool 120 are untreated smooth parts that preferably have reduced dimensions in order to facilitate the passage of the head and avoid contacts with the adjacent teeth. In fact, as illustrated in FIG. 4, it can be noted that the largest part of the tool 120 is that which comprises the working area 121 kept in contact with the wall of the tooth to be ground. The rest of the tool 120 comprising the rod 123 and the retaining ring 124 has a very reduced size, which limits the risks of contact with the adjacent tooth 140.

The body of the tip and the tool are preferably made from a material able to restore and withstand vibratory movements in frequency ranges that may extend from the subsonic ranges to the ultrasonic ranges. Such a material can for example be metal.

Figure 5:
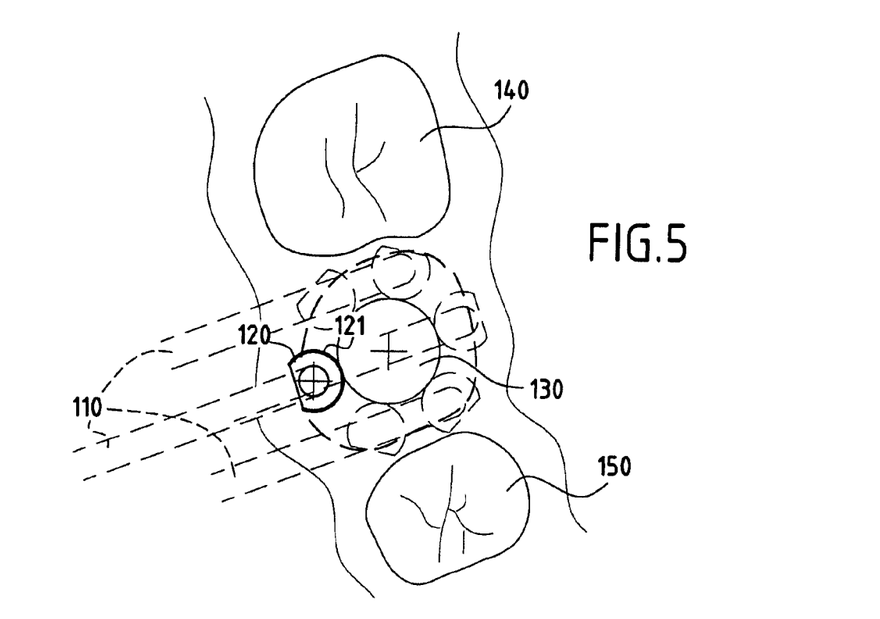
FIG. 5 is a top view showing the different positions taken by the working head of the tip of FIG. 3 during a grinding operation.

By virtue of the free rotation of the tool 120 around the tool holder 112, it is possible to grind a tooth over its entire periphery with a single model of tip. This is illustrated in FIG. 5 which shows the different positions taken by the tool 120 during peripheral grinding of a tooth 130. It should furthermore be noted that the free rotation of the tool 120 makes it possible to keep the body 110 of the tip, and, consequently, the handpiece with which it is coupled, almost always in the same orientation. This allows the practitioner to choose a working position no longer according to the portion of the tooth to be ground but according to the most comfortable working position for him such as for example depending on whether he is right-handed or left-handed.

According to one embodiment of the invention, the tool can be equipped at its end with a guide pin 125. As illustrated in FIG. 4, the guide pin 125 prevents the working area 121 from coming into contact with the gum 160. Thus, the grinding operation for the practitioner becomes less difficult on account of him no longer having to continually control the distance between the end of the tool and the gum. Moreover, as illustrated in FIG. 4, the guide pin also makes it possible to move the gum 160 away.

Furthermore, the position of the pin 125 on the tool and its height make it possible to control the depth of penetration of the working area into the tooth. More precisely, the guide pin 125 makes it possible to control the lateral penetration of the tool into the tooth. This is because, as depicted in FIG. 4, it is no longer possible to remove material once the guide pin 125 is resting on the surface 130b of the tooth 130. Consequently, the guide pin 125 acts as a limit stop which allows the practitioner to grind the tooth with no particular precautions as regards the depth of penetration of the tool since this is limited in advance by virtue of the guide pin.

In a variant embodiment, the guide pin also comprises a working area in order to provide scaling and cleaning of the surface of the tooth 130b and regularisation of the angle 130c.

The tool can have two working areas, a diamond-charged area providing grinding of the tooth and a smooth area providing polishing of the tooth wall.

The shape of the guide pin can be varied. It is preferably cylindrical so as to facilitate guidance of the tool over the tooth. Moreover, depending on the circumstances, two guide pins can be disposed on the tool.

Figure 6A:
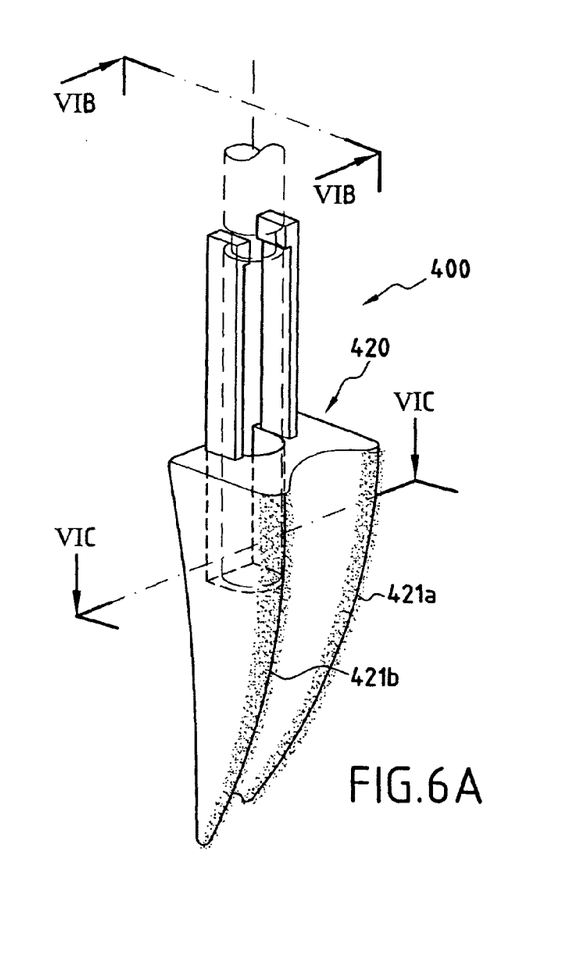
FIGS. 6A, 6B and 6C are respectively a perspective view and two sectional views of a tip in accordance with one embodiment of the invention intended for scaling or polishing tooth or root surfaces, FIG. 6C being a top view showing a tooth and the tool along the section VIC of FIG. 6A.
Figure 6B:
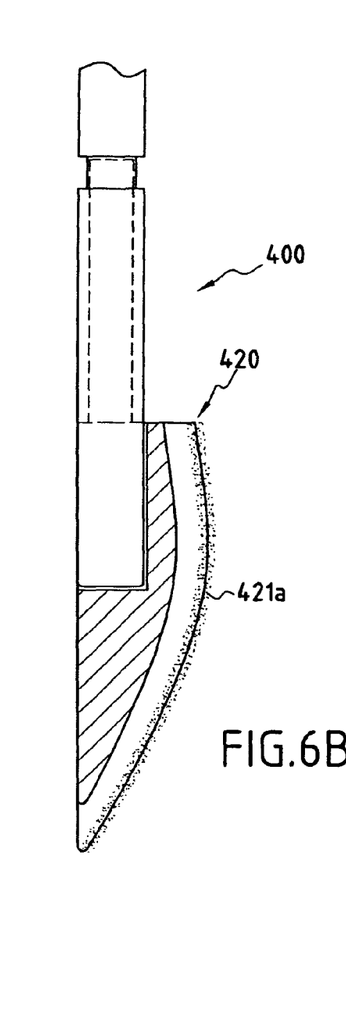
Figure 6C:
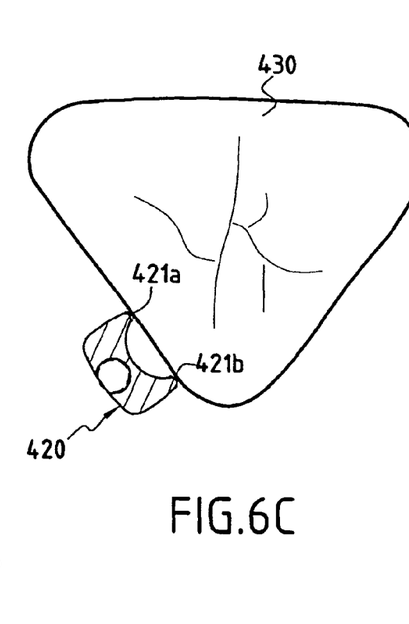

FIGS. 6A to 6C illustrate another embodiment of the invention. The tip 400 depicted in FIGS. 6A and 6B is intended for scaling/polishing. To that end, it comprises a tool 420 comprising two working areas 421a and 421b forming rounded edges, possibly treated and profiled according to the dental anatomy. FIG. 6C highlights the advantage of the two working areas which guide and keep the tool in contact with the surface of the tooth 430 to be treated. This is because, in accordance with the invention, the tool is mounted able to rotate freely with the tool holder. With a tool comprising a single working area and when the practitioner exerts a pressure on the handpiece in order to keep the tool in contact with the tooth which has curved surfaces, keeping the tool on the surface of the tooth can prove difficult (sliding of the tool on the tooth resulting in an undesired rotation of the tool on itself and a loss of contact of the working area with the surface of the tooth). With two working areas spaced apart as illustrated in FIG. 6C, the pressure is distributed over the two working areas (dual point of contact), which makes it possible to have good stability of the bearing of the tool on the tooth, even when the tool is moved. Good contact of the working areas with the tooth is thus guaranteed.

Figure 7A:
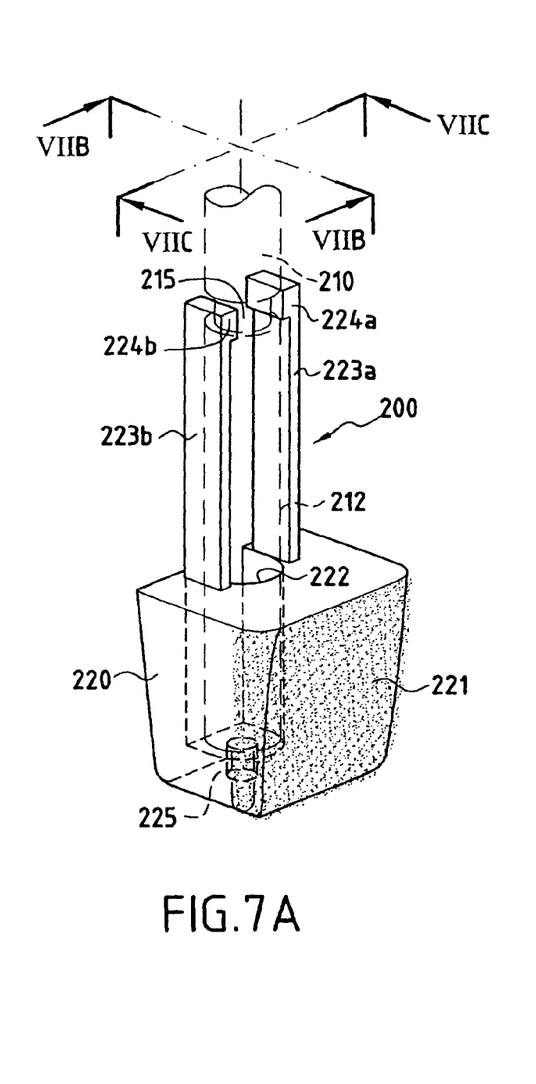
FIGS. 7A, 7B and 7C are respectively a perspective view and two sectional views of a tip in accordance with another embodiment of the invention.
Figures 7B, 7C:
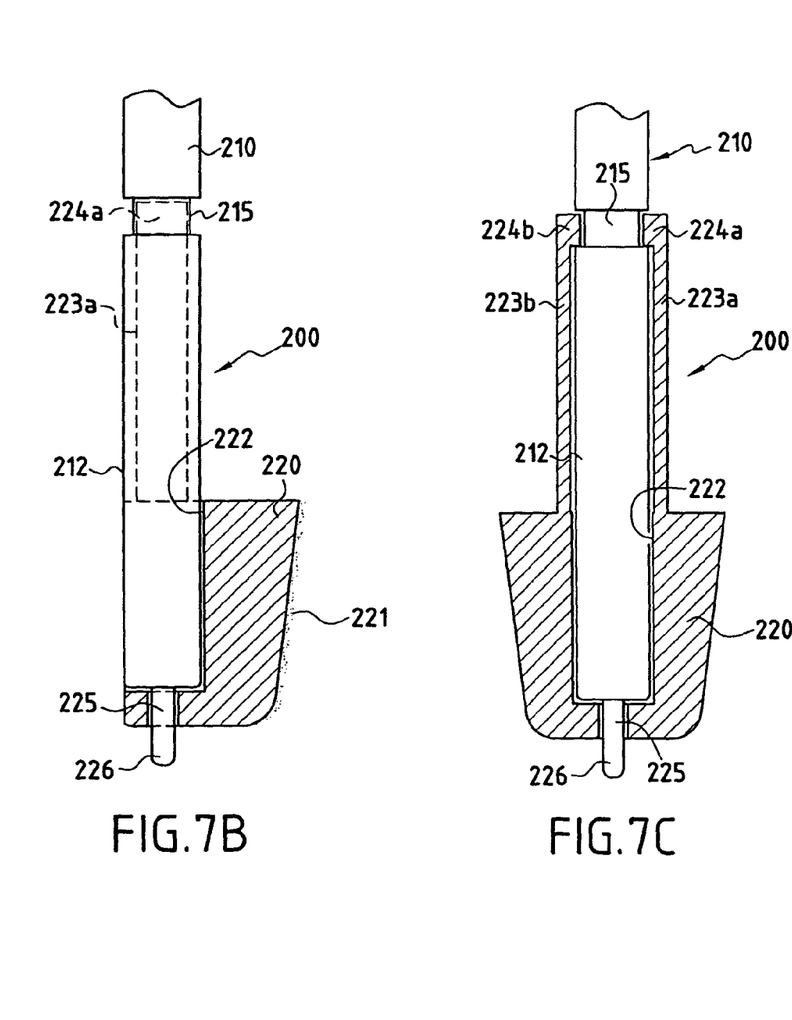

FIGS. 7A to 7C depict another embodiment of a tip according to the invention. The tip 200 presented in these figures differs first of all from that of FIGS. 3 and 4 in that part of the end of the tool holder fixed to the body of the tip 210 completely passes through the tool. More precisely, as illustrated in FIGS. 7A to 7C, the tool holder 212 supports a tool 220 wherein a cavity 222 has been made in order to receive the end of the tool holder 212. This end has a terminal portion 225 that passes through the bottom of the cavity 222. In this embodiment, the part of the terminal portion 225 that goes beyond the tool 220 forms a guide pin 226 that makes it possible to limit the depth of penetration in the same way as described previously in connection with the guide pin 125 of the tool 120.

The other notable difference with the embodiment presented in FIGS. 3 and 4 is with regard to the means used for attaching the tool to the tool holder. This is because, in the embodiment described here, the tool 220 is connected to two rods 223a, 223b each comprising at their end an attachment lug 224a, 224b which fits into a groove 215 made on the tool holder 212. The rods 223a and 223b are elastically deformable so as to facilitate the mounting and/or dismantling of the tool on/from the tool holder.

Just as for the tip described above, the tool 220 comprises a working area 221 which can be either covered with an abrasive material such as diamond, or be smooth or treated and possibly used in association with a solution containing abrasive particles. The tool can obviously also have many other types of shape that persons skilled in the art will envisage without difficulty according to the grinding profile they wish to achieve.

Figure 8A:
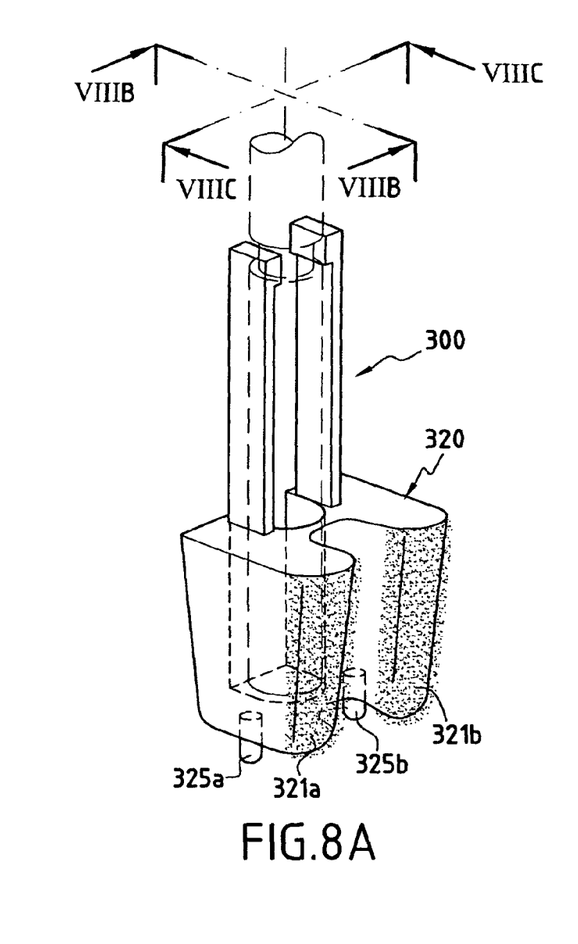
FIGS. 8A, 8B and 8C are respectively a perspective view and two sectional views of a tip in accordance with another embodiment of the invention.
Figure 8B:
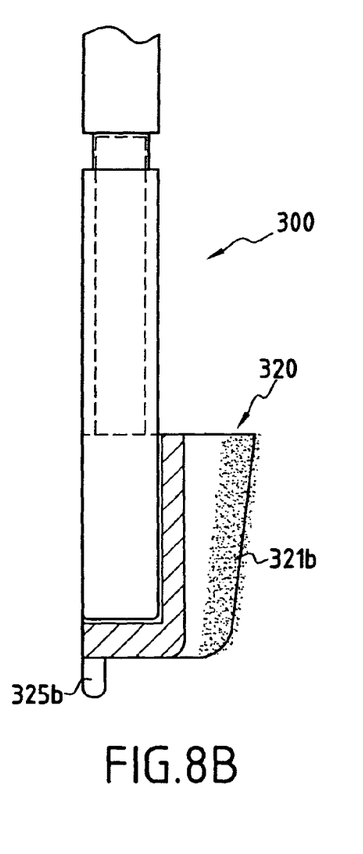
Figure 8C:
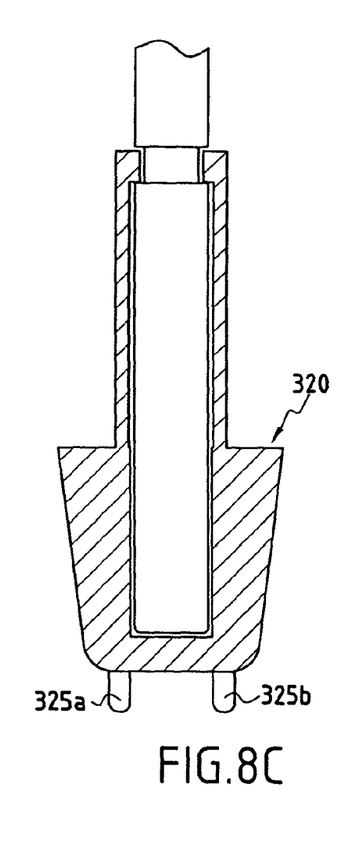

FIGS. 8A to 8C illustrate another variant embodiment of an tip according to the invention. The tip presented in these figures differs from that of FIGS. 7A to 7C in that the tool 320 comprises two working areas 321a and 321b spaced apart by a hollow. This type of tool shape allows good bearing of the working areas on the circumference of the teeth. In this embodiment, the tool 320 furthermore comprises two guide pins 325a and 325b.

In the embodiments described previously, the tool is mounted able to rotate freely around the tool holder. However, the present invention is not limited to this mode of attachment and can also be attached inside the tool holder. In the latter case, the tool is mounted able to rotate freely in the tool holder. In general terms, in accordance with the present invention, the tool must be mounted able to rotate freely with the tool holder.

The tips of the invention can be used with peripheral instruments for dental use such as sound or ultrasound vibration treatment instruments which, through their ergonomics and functionalities, constitute a finished product. An example of this type of instrument is in particular described in the document FR 04 06630. These tips can also be used with instruments presented in the form of modules intended to be integrated (OEM technology) with other modules in dedicated products such as dental surgery workstations.

The invention claimed is:

1. Vibratory tip comprising a body having a first end adapted to be mechanically coupled rigidly with a surgical handpiece generating vibrations and a second end to which there is fixed a tool holder adapted to reproduce the vibrations transmitted by the handpiece, said tip furthermore comprising a tool mounted so as to be freely rotatable relative to the tool holder, the tool connected to the tool holder by at least a rod fixed to a ring, wherein a space is provided between the rod and the tool holder and between the ring and the tool holder, wherein the tool comprises at least one working area at a lower part thereof, and at least one cylindrically shaped guide pin arranged to limit the depth of penetration of the tool, and wherein the at least one guide pin extends from the at least one working area of the tool beyond the lower part thereof.

2. Tip according to claim 1, wherein the tool comprises two working areas adapted to guide the tool and to maintain the tool in contact with a surface to be treated.

3. Tip according to claim 2, wherein each of the least one guide pin comprises a working area.

4. Tip according to claim 2, wherein the guide pin is formed by a terminal portion of the tool holder passing through a bottom of a cavity provided in the tool.

5. Tip according to claim 1, including means for limiting the rotation of the tool within a given angular range.

6. Tip according to claim 1, wherein the tool is detachable and interchangeable.

7. Tip according to claim 1, wherein the tool is connected to the body by an attachment arrangement enabling free rotation of said tool around the tool holder.

8. Tip according to claim 7, wherein the attachment arrangement comprise at least one rod having an end cooperating with a retaining arrangement provided on the tool holder.

9. Tip according to claim 1, wherein the tool comprises a cavity forming a housing for the end of the tool holder.

10. Tip according to claim 9, including a pellet made of flexible material disposed in the bottom of the cavity.

11. Tip according to claim 1, wherein each working area is covered with an abrasive material.

12. Tip according to claim 1, wherein each working area is treated mechanically, chemically or thermally.

13. Tip according to claim 1, wherein each working area has a shape that corresponds to a treatment to be carried out.

14. Ultrasound dental treatment instrument comprising at least one surgical handpiece connected to an ultrasound generator, and at least one tip according to claim 1.

* * * * *